United States Patent [19]

Stach

[11] 3,937,824
[45] Feb. 10, 1976

[54] COMPOSITIONS AND METHODS OF KILLING INSECTS AND ACARIDS USING ALKOXYIMINO CARBAMOYLOXY PHOSPHORUS COMPOUNDS
[75] Inventor: Leonard J. Stach, Riverside, Ill.
[73] Assignee: Velsicol Chemical Corporation, Chicago, Ill.
[22] Filed: Aug. 19, 1974
[21] Appl. No.: 498,496

Related U.S. Application Data
[62] Division of Ser. No. 311,079, Dec. 1, 1974, Pat. No. 3,835,205.

[52] U.S. Cl............................ 424/211; 424/DIG. 8
[51] Int. Cl.² ................................................ A01N 9/36
[58] Field of Search................ 424/211, DIG. 8

[56] References Cited
UNITED STATES PATENTS

| 3,466,316 | 9/1969 | Payne et al. | 260/938 X |
| 3,597,504 | 8/1971 | Richter et al. | 260/944 |
| 3,597,506 | 8/1971 | Richter et al. | 260/944 |

Primary Examiner—Sam Rosen
Assistant Examiner—Allen J. Robinson
Attorney, Agent, or Firm—Robert J. Schwarz; Dietmar H. Olesch

[57] ABSTRACT

This invention discloses compounds of the formula

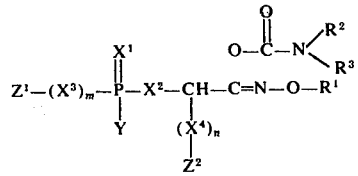

wherein $R^1$ is alkyl; $R^2$ is selected from the group consisting of hydrogen, alkyl, alkenyl, haloalkyl and cycloalkyl; $R^3$ is selected from the group consisting of hydrogen, alkyl, alkenyl, haloalkyl, cycloalkyl and

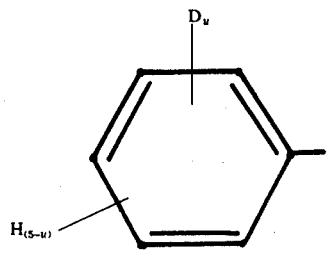

wherein D is selected from the group consisting of alkyl, alkenyl, alkoxy, alkylthio, halogen, haloalkyl, nitro and dialkylamino; and $u$ is an integer from 0 to 3; $X^1$, $X^2$, $X^3$ and $X^4$ are independently selected from the group consisting of oxygen and sulfur; $m$ and $n$ are each integers from 0 to 1; $Z^1$ is selected from the group consisting of alkyl, alkenyl and

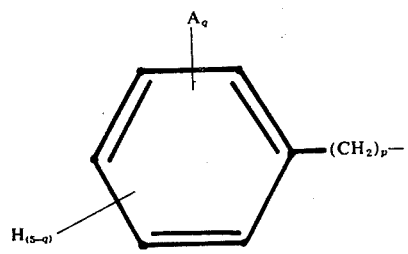

wherein A is selected from the group consisting of alkyl, alkenyl, alkoxy, alkylthio, haloalkyl, halogen, nitro, alkylsulfoxide, alkylsulfone and dialkylamino; and q and p are each integers from 0 to 3; $Z^2$ is selected from the group consisting of hydrogen and $Z^1$, provided that when $Z^2$ is hydrogen then n is zero; and Y is selected from the group consisting of alkyl, alkenyl, alkoxy, alkenyloxy, alkylthio, amino, alkylamino, dialkylamino and

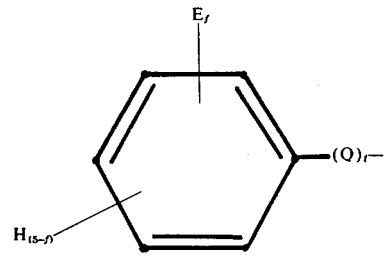

wherein E is selected from the group consisting of alkyl, alkenyl, alkoxy, alkylthio, halogen, nitro, alkylsulfoxide, alkylsulfone and dialkylamino; $f$ is an integer from 0 to 3; Q is selected from the group consisting of oxygen, sulfur, alkylene, alkyleneoxy and alkylenethio; and $t$ is an integer from 0 to 1. The above compounds are useful as insecticides and acaricides.

3 Claims, No Drawings

COMPOSITIONS AND METHODS OF KILLING INSECTS AND ACARIDS USING ALKOXYIMINO CARBAMOYLOXY PHOSPHORUS COMPOUNDS

This application is a division of application Ser. No. 311,079, filed Dec. 1, 1974, now U.S. Pat. No. 3,835,205, issued Sept. 10, 1974.

This invention relates to new compositions of matter and more specifically relates to new chemical compounds of the formula

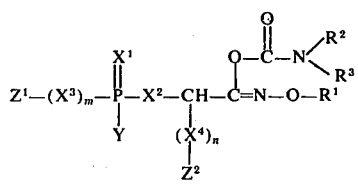

wherein $R^1$ is alkyl; $R^2$ is selected from the group consisting of hydrogen, alkyl, alkenyl, haloalkyl and cycloalkyl; $R^3$ is selected from the group consisting of hydrogen, alkyl, alkenyl, haloalkyl, cycloalkyl and

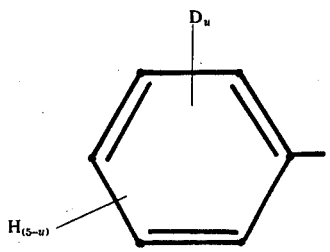

wherein D is selected from the group consisting of alkyl, alkenyl, alkoxy, alkylthio, halogen, haloalkyl, nitro and dialkylamino; and u is an integer from 0 to 3; $X^1$, $X^2$, $X^3$ and $X^4$ are independently selected from the group consisting of oxygen and sulfur; m and n are each integers from 0 to 1; $Z^1$ is selected from the group consisting of alkyl, alkenyl and

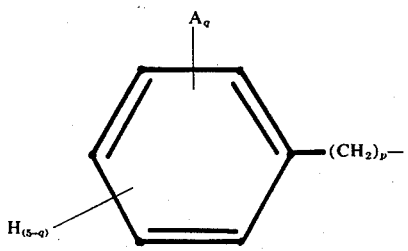

wherein A is selected from the group consisting of alkyl, alkenyl, alkoxy, alkylthio, haloalkyl, halogen, nitro, alkylsulfoxide, alkylsulfone and dialkylamino; and q and p are each integers from 0 to 3; $Z^2$ is selected from the group consisting of hydrogen and $Z^1$, provided that when $Z^2$ is hydrogen then n is zero; and Y is selected from the group consisting of alkyl, alkenyl, alkoxy, alkenyloxy, alkylthio, amino, alkylamino, dialkylamino and

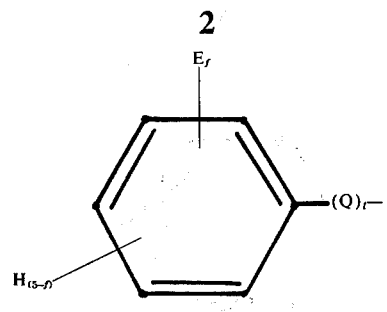

wherein E is selected from the group consisting of alkyl, alkenyl, alkoxy, alkylthio, halogen, nitro, alkylsulfoxide, alkylsulfone and dialkylamino; $f$ is an integer from 0 to 3; Q is selected from the group consisting of oxygen, sulfur, alkylene, alkyleneoxy and alkylenethio; and t is an integer from 0 to 1.

The compounds of the present invention are unexpectedly useful as insecticides and acaricides.

In a preferred embodiment of this invention $R^1$ is lower alkyl; $R^2$ is selected from the group consisting of hydrogen, lower alkyl, lower alkenyl and lower haloalkyl; $R^3$ is selected from the group consisting of hydrogen, lower alkyl, lower alkenyl, lower haloalkyl, cycloalkyl of from 3 to 7 carbon atoms and

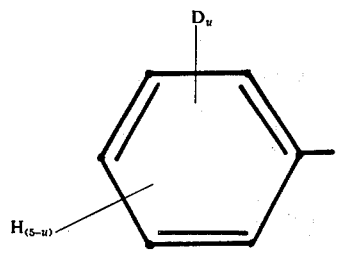

wherein D is selected from the group consisting of lower alkyl, lower alkenyl, lower alkoxy, lower alkylthio, chlorine, bromine, fluorine, lower haloalkyl, nitro and di(lower alkyl)-amino; u is an integer from 0 to 3; $Z^1$ is selected from the group consisting of lower alkyl, lower alkenyl and

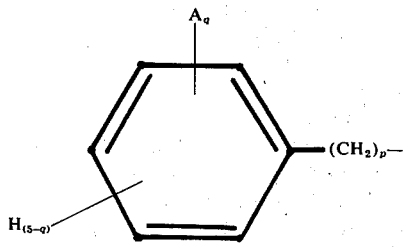

wherein A is selected from the group consisting of lower alkyl, lower alkenyl, lower alkoxy, lower alkylthio, lower haloalkyl, chlorine, bromine, fluorine, nitro, lower alkylsulfoxide, lower alkylsulfone and di(lower alkyl)amino; and q and p are each integers from 0 to 3; $Z^2$ is selected from the group consisting of hydrogen and the preferred $Z^1$; and Y is selected from the group consisting of lower alkyl, lower alkenyl, lower alkoxy, lower alkenyloxy, lower alkylthio, amino, lower alkylamino, di(lower alkyl)amino and

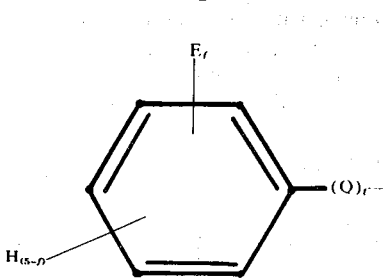

wherein E is selected from the group consisting of lower alkyl, lower alkenyl, lower alkoxy, lower alkylthio, chlorine, bromine, fluorine, nitro, lower alkylsulfoxide, lower alkylsulfone and di(lower alkyl)amino; $f$ is an integer from 0 to 3; Q is selected from the group consisting of oxygen, sulfur, lower alkylene, lower alkyleneoxy and lower alkylenethio; and $t$ is an integer from 0 to 1.

The term lower as used herein designates a straight or branched carbon chain of up to six carbon atoms.

The compounds of the present invention can be readily prepared by reacting a compound of the formula

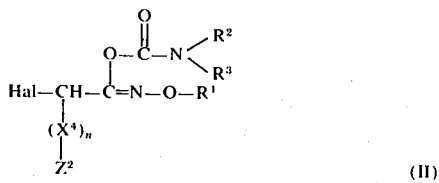

wherein Hal designates halogen, preferably chlorine or bromine and $X^4$, $n$, $Z^2$, $R^1$, $R^2$ and $R^3$ are as heretofore described, with a compound of the formula

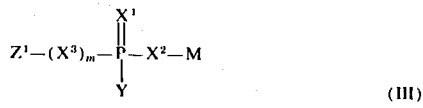

wherein M is an alkali metal such as sodium or potassium and $Z^1$, $X^1$, $X^2$, $X^3$, $m$ and Y are as heretofore described. This reaction can be effected by combining the reactants in an organic reaction medium such as methyl ethyl ketone and optionally in the presence of a catalytic amount of potassium iodide. The reactant can then be heated at the reflux temperature of the mixture for a period of from about 2 to about 18 hours. After this time the mixture can be filtered to remove the inorganic salt which has formed. The remaining filtrate can then be stripped of solvent by evaporation to yield the desired product which can be used as such or can be further purified by common techniques in the art such as washing, distillation and the like.

The compounds of formula II can be prepared by reacting a compound of the formula

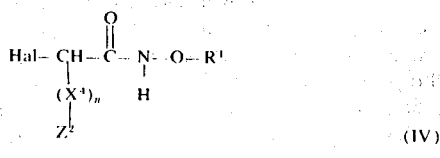

wherein Hal designates halogen and $X^4$, $n$, $Z^2$ and $R^1$ are as heretofore described with about an equimolar amount of a carbamoyl chloride of the formula

wherein $R^2$ and $R^3$ are as heretofore defined. This reaction can be effected by combining the reactants in an inert organic reaction medium in the presence of an acid acceptor such as a tertiary amine or alkali metal carbonate. The reaction mixture can be heated at a temperature of from about 50°C to the reflux temperature of the mixture for a period of from about 1/2 to about 18 hours. After this time the reaction mixture can be filtered to remove the acid acceptor halide and can then be stripped of solvent to yield the desired product as a residue. The product can then be used as such or can be further purified by conventional techniques well known in the art.

The compounds of formula II wherein at least one of $R^2$ and $R^3$ is hydrogen can also be prepared by reacting a compound of formula IV with an isocyanate of the formula $$R^3—N=C=O \quad (VI)$$

wherein $R^3$ is as heretofore defined. This reaction can be effected by slowly adding a solution of the isocyanate of formula VI in an inert solvent such as benzene to a solution of the compound of formula IV in an inert organic solvent such as benzene in the presence of a catalytic amount of dibutyltin dilaurate. After the addition is completed the reaction mixture can be heated at a temperature of up to the reflux temperature of the mixture for a period of up to several hours to ensure completion of the reaction. After this time the reaction mixture can be distilled to remove the solvent and unreacted starting materials to yield the desired product. This product can then be used as such or can be further purified by standard procedures.

The compounds of formula III are known in the art and can be prepared by the methods described by Malatesta and Pizotti, Chimica e Industria (Milan) 27, 6–10 (1945); and Melnikov and Grapov, Zhur. Vsesoyuz Khim. Obschchestva in D.I. Mendeleeva, 6 No. 1; 119-20 (1961).

Exemplary useful compounds of formula IV for preparing the compounds of the present invention are N-methoxy-α-chloroacetamide, N-ethoxy-α-bromoacetamide, N-isopropoxy-α-chloroacetamide, N-butoxy-α-chloroacetamide, N-pentyloxy-α-chloroacetamide, N-hexyloxy-α-chloroacetamide, N-methoxy-α-chloropropionamide, N-ethoxy-α-chlorobutyramide, N-methoxy-α-chloropentanamide, N-methoxy-α-chlorohexanamide, N-propoxy-α-methoxy-α-chloroacetamide, N-t-butoxy-α-ethoxy-α-chloroacetamide, N-methoxy-α-methylthioacetamide, N-methoxy-α-pentoxy-α-chloroacetamide, N-methoxy-α-phenyl-α-chloroacetamide, N-methoxy-α-phenoxy-α-chloroacetamide, N-methoxy-α-(3,4-dichlorophenyl)-α-chloroacetamide, N-methoxy-α-(2-methoxyphenyl)-α-chloroacetamide, N-methoxy-α-(4-methylphenyl)-α-chloroacetamide, N-methoxy-α-(4-dimethylaminophenyl)-α-chloroacetamide, N-ethoxy-α-(4-nitrophenyl)-α-chloroacetamide, N-methoxy-α-benzyl-α-chloroacetamide, N-methoxy- -(4-methylsulfinylphenyl)-α-chloroacetamide, N-methoxy-α-(4-methylsulfonylphenyl)-α-chloroacetamide and the like.

Exemplary useful carbamoyl chlorides of formula V are carbamoyl chloride, N-methylcarbamoyl chloride, N,N-dimethylcarbamoyl chloride, N-ethylcarbamoyl chloride, N-propylcarbamoyl chloride, N-butylcarbamoyl chloride, N-pentylcarbamoyl chloride, N-hexylcarbamoyl chloride, N-allylcarbamoyl chloride, N-pent-4-enylcarbamoyl chloride, N-chloromethylcarbamoyl chloride, N-β-chloroethylcarbamoyl chloride, N-β-bromoethylcarbamoyl chloride, N-β,β,β-trichloroethylcarbamoyl chloride, N-cyclopropylcarbamoyl chloride, N-cyclopentylcarbamoyl chloride, N-cyclohexylcarbamoyl chloride, N-cycloheptylcarbamoyl chloride, N-phenylcarbamoyl chloride, N-(4-chlorophenyl)carbamoyl chloride, N-(4-bromophenyl)carbamoyl chloride, N-(2-methyl-4-trifluoromethylphenyl)carbamoyl chloride, N-(2-methoxyphenyl)carbamoyl chloride, N-(3-nitrophenyl)carbamoyl chloride, N-(2-dimethylaminophenyl)carbamoyl chloride, N-(3-methylthiophenyl)carbamoyl chloride, N-(4-allylphenyl)carbamoyl chloride, N-methyl-N-cyclohexylcarbamoyl chloride, N,N-dimethylcarbamoyl chloride, N,N-dihexylcarbamoyl chloride, N-methyl-N-(3,4-dichlorophenyl)-carbamoyl chloride and the like.

Exemplary useful isocyanates of formula VI are methyl isocyanate, ethyl isocyanate, propyl isocyanate, butyl isocyanate, pentyl isocyanate, hexyl isocyanate, phenyl isocyanate, 4-fluorophenyl isocyanate, cyclohexyl isocyanate, cyclobutyl isocyanate, cyclopropyl isocyanate, 3-ethylphenyl isocyanate, 2-ethoxyphenyl isocyanate and the like.

The manner in which the compounds of the present invention can be prepared is more specifically illustrated in the following examples.

EXAMPLE 1

Preparation of 1-Chloro-2-(N-methyl-carbamoyloxy)-2-methoxyiminoethane

N-Methoxychloroacetamide (3.5 grams), benzene (60 ml) and dibutyltin dilaurate (1 drop) were charged into a glass reaction vessel equipped with a mechanical stirrer, thermometer and reflux condenser. Methyl isocyanate (2.0 grams) dissolved in benzene (15 ml) was added dropwise to the reaction mixture at room temperature and with stirring. After the addition was completed the reaction mixture was heated at reflux, with stirring for a period of about 2 hours. After this time the reaction mixture was distilled to remove benzene and unreacted isocyanate leaving an oily residue. The residue was subjected to vacuum (0.1 mm Hg) whereupon it solidified. The solid was recrystallized from a carbon tetrachloride-hexane mixture to yield a white crystalline solid. The solid was washed with hexane and dried to yield the desired product 1-chloro-2-(N-methylcarbamoyloxy)-2-methoxyiminoethane having a melting point of 80°–82°C.

EXAMPLE 2

Preparation of S-[2-(N-Methylcarbamoyloxy)-2-methoxyiminoethyl]O,O-Diethel Thiolothionophosphate 1-Chloro-2-(N-methylcarbamoyloxy)-2-methoxyiminoethane (4.32 grams; 0.02 mole), methyl ethyl ketone (70 ml), potassium O,O-diethel thiolothionophosphate (6.72 grams; 0.03 mole) and a few crystals of potassium iodide were charged into a glass reaction flask equipped with a mechanical stirrer, thermometer and reflux condenser. The reaction mixture was then heated at reflux overnight. After this time the reaction mixture was cooled to room temperature and was filtered to remove inorganic salts. The salts were washed with acetone and the washings were combined with the filtrate. The resulting solution was stripped of solvents in a rotary evaporator. The remaining residue was dissolved in ether and the ether solution was washed with water and dried over anhydrous magnesium sulfate. The dried solution was filtered and stripped of ether on a steam bath to yield a pale yellow oil. This oil was dried under a vacuum (0.10 mm Hg) for a period of about 10 minutes and passed through a sintered glass filter to yield the desired product S-[2-(N-methylcarbamoyloxy)-2-methoxyiminoethyl] O,O-diethel thiolothionophosphate as a pale yellow oil.

EXAMPLE 3

Preparation of S-[2-(N-Methylcarbamoyloxy)-2-methoxy-iminoethyl] O-Ethyl N-Isopropylthiolophosphoramidate 1-Chloro-2-(N-methylcarbamoyloxy)-2-methoxyiminoethane (9.00 grams; 0.05 mole), methyl ethyl ketone (70 ml), potassium O-ethyl N-isopropylthiolophosphoramidate (13.2 grams; 0.06 mole) and a few crystals of potassium iodide were charged into a glass reaction flask equipped with a mechanical stirrer, thermometer and reflux condenser. The reaction mixture was then heated at reflux for a period of about 24 hours. After this time the reaction mixture was cooled to room temperature and was filtered to remove inorganic salts. The salts were washed with acetone and the washings were combined with the filtrate. The resulting solution was stripped of solvent in a rotary evaporator. The remaining residue was dissolved in methylene chloride and the methylene chloride solution was washed with water and dried over anhydrous magnesium sulfate. The dried solution was filtered and stripped of methylene chloride on a steam bath to yield an oil. This oil was dried further under a vacuum (0.20 mm Hg) for a period of fifteen minutes to yield the desired product S-[2-(N-methylcarbamoyloxy)-2-methoxyiminoethyl] O-ethyl N-isopropylthiolophosphoramidate, as a red oil.

EXAMPLE 4

Preparation of 1-Chloro-2-(N-isopropylcarbamoyloxy)-2-ethoxyiminoethane

N-Ethoxychloroacetamide (6.9 grams; 0.05 mole), benzene (70 ml) and dibutyltin dilaurate (1 drop) are charged into a glass reaction flask equipped with a mechanical stirrer, thermometer and reflux condenser. Isopropylisocyanate (5.1 grams; 0.06 mole) dissolved in benzene (20 ml) is incrementally added to the reaction mixture, with stirring, at room temperature. After the addition is completed the reaction mixture is heated at reflux for a period of about 2 hours. After this time the reaction mixture is distilled to remove benzene and unreacted starting material thereby yielding the desired product 1-chloro-2-(N-isopropylcarbamoyloxy)-2-ethoxyiminoethane.

EXAMPLE 5

Preparation of
S-[2-(N-Isopropylcarbamoyloxy)-2-ethoxyiminoethyl]
O-Methyl N-t-Butylthiolophosphoramidate 1-Chloro-2-(N-isopropylcarbamoyloxy)-2-ethoxyiminoethane (4.5 grams; 0.02 mole), methyl ethyl ketone (50 ml), potassium O-methyl N-t-butylthiolophosphoramidate (6.6 grams; 0.03 mole) and a few crystals of potassium iodide are charged into a glass reaction flask equipped with a mechanical stirrer, thermometer and reflux condenser. The reaction mixture is then heated at reflux for a period of about 6 hours. After this time the reaction mixture is cooled to room temperature and is filtered to remove inorganic salts. The salts are washed with acetone and the washings combined with the filtrate. The resulting solution is stripped of solvents in a rotary evaporator. The remaining residue is dissolved in ether and the ether solution is washed with water and dried over anhydrous magnesium sulfate. The dried solution is filtered and stripped of ether to yield the desired product S-[2-(N-isopropylcarbamoyloxy)-2-ethoxyiminoethyl] O-methyl N-t-butylthiolophosphoramidate.

EXAMPLE 6

Preparation of
1-Chloro-2-(N-phenyl-carbamoyloxy)-2-propoxyiminoethane

N-Propoxychloroacetamide (15.1 grams; 0.1 mole), benzene (80 ml) and dibutyltin dilaurate (1 drop) are charged into a glass reaction flask equipped with a mechanical stirrer, thermometer and reflux condenser. Phenylisocyanate (12.1 grams; 0.12 mole) dissolved in benzene (25 ml) is incrementally added to the reaction mixture, with stirring, at room temperature. After the addition is completed the reaction mixture is heated at reflux for a period of about 20 hours. After this time the reaction mixture is distilled to remove benzene and unreacted starting material thereby yielding the desired product 1-chloro-2-(N-phenylcarbamoyloxy)-2-propoxyiminoethane.

EXAMPLE 7

Preparation of
O-[2-(N-Phenylcarbamoyloxy)-2-propoxyiminoethyl]
Ethyl-N-isopropylphosphonamidate 1-Chloro-2-(N-phenylcarbamoyloxy)-2-propoxyiminoethane (13.5 grams; 0.05 mole), methyl ethyl ketone (60 ml), potassium ethyl-N-isopropylphosphonamidate (9.4 grams; 0.05 mole) and a few crystals of potassium iodide are charged into a glass reaction flask equipped with a mechanical stirrer, thermometer and reflux condenser. The reaction mixture is then heated at reflux for a period of about 6 hours. After this time the reaction mixture is cooled to room temperature and is filtered to remove inorganic salts. The salts are washed with acetone and the washings combined with the filtrate. The resulting solution is stripped of solvents in a rotary evaporator. The remaining residue is dissolved in ether and the ether solution is washed with water and dried over anhydrous magnesium sulfate. The dried solution is filtered and stripped of ether to yield the desired product O-[2-(N-phenylcarbamoyloxy)-2-propoxyiminoethyl] ethyl-N-isopropylphosphonamidate.

EXAMPLE 8

Preparation of
1-Chloro-2-(N-3,4-dichlorophenylcarbamoyloxy)-2-methoxyiminoethane N-Methoxychloroacetamide (12.3 grams; 0.1 mole), benzene (50 ml) and dibutyltin dilaurate (1 drop) are charged into a glass reaction flask equipped with a mechanical stirrer, thermometer and reflux condenser. 3,4-Dichlorophenylisocyanate (27.6 grams; 0.1 mole) dissolved in benzene (40 ml) is incrementally added to the reaction mixture with stirring, at room temperature. After the addition is completed the reaction mixture is heated at reflux for a period of about 4 hours. After this time the reaction mixture is distilled to remove benzene and unreacted starting material thereby yielding the desired product 1-chloro-2-(N-3,4-dichlorophenylcarbamoyloxy)-2-methoxyiminoethane.

EXAMPLE 9

Preparation of
S-[2-(N-3,4-Dichlorophenylcarbamoyloxy)-2-methoxyiminoethyl] S-Hexyl
N,N-Dimethyldithiolophosphoramidate 1-Chloro-2-(N-3,4-dichlorophenylcarbamoyloxy)-2-methoxyiminoethane (14.8 grams; 0.05 mole), methyl ethyl ketone (60 ml), potassium S-hexyl N,N-dimethyldithiolophosphoramidate (13.9 grams; 0.05 mole) and a few crystals of potassium iodide are charged into a glass reaction flask equipped with a mechanical stirrer, thermometer and reflux condenser. The reaction mixture is then heated at reflux for a period of about 6 hours. After this time the reaction mixture is cooled to room temperature and is filtered to remove inorganic salts. The salts are washed with acetone and the washings combined with the filtrate. The resulting solution is stripped of solvents in a rotary evaporator. The remaining residue is dissolved in ether and the ether solution is washed with water and dried over anhydrous magnesium sulfate. The dried solution is filtered and stripped of ether to yield the desired product S-[2-(N-3,4-dichlorophenylcarbamoyloxy)-2-methoxyiminoethyl] S-hexyl N,N-dimethyldithiolophosphoramidate.

EXAMPLE 10

Preparation of
1-Chloro-2-(N-cyclopropylcarbamoyloxy)-2-ethoxyiminoethane

N-Ethoxychloroacetamide (13.7 grams; 0.1 mole), benzene (60 ml) and dibutyltin dilaurate (1 drop) are charged into a glass reaction flask equipped with a mechanical stirrer, thermometer and reflux condenser. Cyclopropylisocyanate (10 grams; 0.12 mole) dissolved in benzene (20 ml) is incrementally added to the reaction mixture, with stirring, at room temperature. After the addition is completed the reaction mixture is heated at reflux for a period of about 2 hours. After this time the reaction mixture is distilled to remove benzene and unreacted starting material thereby yielding the desired product 1-chloro-2-(N-cyclopropylcarbamoyloxy)-2-ethoxyiminoethane.

EXAMPLE 11

Preparation of
O-[2-(N-Cyclopropylcarbamoyloxy)-2-ethoxyiminoethyl]
2-Methylphenyl(4-bromophenyl)thionophosphinate 1-Chloro-2-(N-cyclopropylcarbamoyloxy)-2-ethoxyiminoethane (11 grams; 0.05 mole), methyl ethyl ketone (80 ml), potassium 2-methylphenyl(4-bromophenyl)thionophosphinate (17 grams; 0.05 mole) and a few crystals of potassium iodide are charged into a glass reaction flask equipped with a mechanical stirrer, thermometer and reflux condenser. The reaction mixture is then heated at reflux for a period of about 8 hours. After this time the reaction mixture is cooled to room temperature and is filtered to remove inorganic salts. The salts are washed with acetone and the washings combined with the filtrate. The resulting solution is stripped of solvents in a rotary evaporator. The remaining residue is dissolved in ether and the ether solution is washed with water and dried over anhydrous magnesium sulfate. The dried solution is filtered and stripped of ether to yield the desired product O-[2-(N-cyclopropylcarbamoyloxy)-2-ethoxyiminoethyl] 2-methylphenyl(4-bromophenyl)thionophosphinate.

EXAMPLE 12

Preparation of
1-Chloro-2-(N-β-chloroethylcarbamoyloxy)-2-hexyloxyiminoethane

N-Hexyloxychloroacetamide (19 grams; 0.1 mole), benzene (100 ml) and dibutyltin dilaurate (1 drop) are charged into a glass reaction flask equipped with a mechanical stirrer, thermometer and reflux condenser. β-Chloroethylisocyanate (12.6 grams; 0.12 mole) dissolved in benzene (25 ml) is incrementally added to the reaction mixture, with stirring, at room temperature. After the addition is completed the reaction mixture is heated at reflux for a period of about 3 hours. After this time the reaction mixture is distilled to remove benzene and unreacted starting material thereby yielding the desired product 1-chloro-2-(N-β-chloroethylcarbamoyloxy)-2-hexyloxyiminoethane.

EXAMPLE 13

Preparation of
S-[2-(N-β-Chloroethylcarbamoyloxy)-2-hexyloxyiminoethyl] O-(4-Methylthiophenyl)
Methylthiolophosphonate 1-Chloro-2-(N-β-chloroethylcarbamoyloxy)-2-hexyloxyiminoethane (15 grams; 0.05 mole), methyl ethyl ketone (75 ml), potassium O-(4-methylthiophenyl) methylthiolophosphonate (13.6 grams; 0.05 mole) and a few crystals of potassium iodide are charged into a glass reaction flask equipped with a mechanical stirrer, thermometer and reflux condenser. The reaction mixture is then heated at reflux for a period of about 5 hours. After this time the reaction mixture is cooled to room temperature and is filtered to remove inorganic salts. The salts are washed with acetone and the washings combined with the filtrate. The resulting solution is stripped of solvents in a rotary evaporator. The remaining residue is dissolved in ether and the ether solution is washed with water and dried over anhydrous magnesium sulfate. The dried solution is filtered and stripped of ether to yield the desired product S-[2-(N-β-chloroethylcarbamoyloxy)-2-hexyloxyiminoethyl] O-(4-methylthiophenyl) methylthiolophosphonate.

EXAMPLE 14

Preparation of
1-Chloro-2-[N-(2-methoxyphenyl)-carbamoyloxy]-2-methoxyiminoethane N-Methoxychloroacetamide (12.3 grams; 0.1 mole), benzene (60 ml) and dibutyltin dilaurate (1 drop) are charged into a glass reaction flask equipped with a mechanical stirrer, thermometer and reflux condenser. 2-Methoxyphenylisocyanate (15 grams; 0.1 mole) dissolved in benzene (30 ml) is incrementally added to the reaction mixture, with stirring, at room temperature. After the addition is completed the reaction mixture is heated at reflux for a period of about 3 hours. After this time the reaction mixture is distilled to remove benzene and unreacted starting material thereby yielding the desired product 1-chloro-2-[N-(2-methoxyphenyl)carbamoyloxy]-2-methoxyiminoethane.

EXAMPLE 15

Preparation of
S-{2-[N-(2-Methoxyphenyl)carbamoyloxy]-2-methoxyiminoethyl} O-(4-Trifluoromethylphenyl)
Phosphoramidate 1-Chloro-2-[N-(2-methoxyphenyl)carbamoyloxy]-2-methoxyiminoethane (13.6 grams; 0.05 mole), methyl ethyl ketone (60 ml), potassium O-(4-trifluoromethylphenyl) phosphoramidate (14.7 grams; 0.05 mole) and a few crystals of potassium iodide are charged into a glass reaction flask equipped with a mechanical stirrer, thermometer and reflux condenser. The reaction mixture is then heated at reflux for a period of about 6 hours. After this time the reaction mixture is cooled to room temperature and is filtered to remove inorganic salts. The salts are washed with acetone and the washings combined with the filtrate. The resulting solution is stripped of solvents in a rotary evaporator. The remaining residue is dissolved in ether and the ether solution is washed with water and dried over anhydrous magnesium sulfate. The dried solution is filtered and stripped of ether to yield the desired product S-{2-[N-(2-methoxyphenyl)-carbamoyloxy]-2-methoxyiminoethyl} O-(4-trifluoromethylphenyl) phosphoramidate.

EXAMPLE 16

Preparation of
1-Chloro-2-[N-(2-methyl-4-methylthiophenyl)carbamoyloxy]-2-methoxyiminoethane N-Methoxychloroacetamide (12.3 grams; 0.1 mole), benzene (60 ml) and dibutyltin dilaurate (1 drop) are charged into a glass reaction flask equipped with a mechanical stirrer, thermometer and reflux condenser. 2-Methyl-4-methylthiophenylisocyanate (21.5 grams; 0.12 mole) dissolved in benzene (30 ml) is incrementally added to the reaction mixture, with stirring, at room temperature. After the addition is completed the reaction mixture is heated at reflux for a period of about 2 hours. After this time the reaction mixture is distilled to remove benzene and unreacted starting material thereby yielding the desired product 1-chloro-2-[N-(2-methyl-4-methylthiophenyl)carbamoyloxy]-2-methoxyiminoethane.

EXAMPLE 17

Preparation of
S-{2-[N-(2-Methyl-4-methylthiophenyl)carbamoyloxy]-2-methoxyiminoethyl} O-(2-Dimethylaminophenyl) O-(4-Nitrophenyl) Thiolothionophosphate 1-Chloro-2-[N-(2-methyl-4-methylthiophenyl)carbamoyloxy]-2-methoxyiminoethane (15.1 grams; 0.05 mole), methyl ethyl ketone (75 ml), potassium O-(2-dimethylaminophenyl) O-(4-nitrophenyl) thiolothionophosphate (19.6 grams; 0.05 mole) and a few crystals of potassium iodide are charged into a glass reaction flask equipped with a mechanical stirrer, thermometer and reflux condenser. The reaction mixture is then heated at reflux for a period of about 8 hours. After this time the reaction mixture is cooled to room temperature and is filtered to remove inorganic salts. The salts are washed with acetone and the washings combined with the filtrate. The resulting solution is stripped of solvents in a rotary evaporator. The remaining residue is dissolved in ether and the ether solution is washed with water and dried over anhydrous magnesium sulfate. The dried solution is filtered and stripped of ether to yield the desired product S-{2-[N-(2-methyl-4-methylthiophenyl)carbamoyloxy]-2-methoxyiminoethyl } O-(2-dimethylaminophenyl) O-(4-nitrophenyl) thiolothionophosphate.

EXAMPLE 18

Preparation of
1-Chloro-2-(N-4-nitrophenyl-carbamoyloxy)-2-methoxyiminoethane

N-Methoxychloroacetamide (12.3 grams; 0.1 mole), benzene (80 ml) and dibutyltin dilaurate (1 drop) are charged into a glass reaction flask equipped with a mechanical stirrer, thermometer and reflux condenser. 4-Nitrophenylisocyanate (16.4 grams; 0.1 mole) dissolved in benzene (30 ml) is incrementally added to the reaction mixture, with stirring, at room temperature. After the addition is completed the reaction mixture is heated at reflux for a period of about 4 hours. After this time the reaction mixture is distilled to remove benzene and unreacted starting material thereby yielding the desired product 1-chloro-2-(N-4-nitrophenylcarbamoyloxy)-2-methoxyiminoethane.

EXAMPLE 19

Preparation of
S-[2-(N-4-Nitrophenylcarbamoyloxy)-2-methoxyiminoethyl] S-(2-Methoxyphenyl) 4-Methylsulfonylphenyldithiolophosphonate 1-Chloro-2-(N-4-nitrophenylcarbamoyloxy-2-methoxyiminoethane (14.3 grams; 0.05 mole), methyl ethyl ketone (100 ml), potassium S-(2-methoxyphenyl) 4-methylsulfonylphenyldithiolophosphonate (20.6 grams; 0.05 mole) and a few crystals of potassium iodide are charged into a glass reaction flask equipped with a mechanical stirrer, thermometer and reflux condenser. The reaction mixture is then heated at reflux for a period of about 12 hours. After this time the reaction mixture is cooled to room temperature and is filtered to remove inorganic salts. The salts are washed with acetone and the washings combined with the filtrate. The resulting solution is stripped of solvents in a rotary evaporator. The remaining residue is dissolved in ether and the ether solution is washed with water and dried over anhydrous magnesium sulfate. The dried solution is filtered and stripped of ether to yield the desired product S-[2-(N-4-nitrophenylcarbamoyloxy)-2-methoxyiminoethyl] S-(2-methoxyphenyl) 4-methylsulfonylphenyldithiolophosphonate.

EXAMPLE 20

Preparation of
1-Chloro-2-(N-3-allylphenyl-carbamoyloxy)-2-methoxyiminoethane

N-Methoxychloroacetamide (12.3 grams; 0.1 mole), benzene (80 ml) and dibutyltin dilaurate (1 drop) are charged into a glass reaction flask equipped with a mechanical stirrer, thermometer and reflux condenser. 3-Allylphenylisocyanate (16 grams; 0.1 mole) dissolved in benzene (30 ml) is incrementally added to the reaction mixture, with stirring, at room temperature. After the addition is completed the reaction mixture is heated at reflux for a period of about 2 hours. After this time the reaction mixture is distilled to remove benzene and unreacted starting material thereby yielding the desired product 1-chloro-2-(N-3-allylphenylcarbamoyloxy)-2-methoxyiminoethane.

EXAMPLE 21

Preparation of
O-[2-(N-3-Allylphenylcarbamoyloxy)-2-methoxyiminoethyl]
3-Methylsulfinylphenyl(4-methylthiophenyl)phosphinate 1-Chloro-2-(N-3-allylphenylcarbamoyloxy)-2-methoxyiminoethane (14.1 grams; 0.05 mole), methyl ethyl ketone (100 ml), potassium 3-methylsulfinylphenyl(4-methylthiophenyl)phosphinate (18.2 grams; 0.05 mole) and a few crystals of potassium iodide are charged into a glass reaction flask equipped with a mechanical stirrer, thermometer and reflux condenser. The reaction mixture is then heated at reflux for a period of about 6 hours. After this time the reaction mixture is cooled to room temperature and is filtered to remove inorganic salts. The salts are washed with acetone and the washings combined with the filtrate. The resulting solution is stripped of solvents in a rotary evaporator. The remaining residue is dissolved in ether and the ether solution is washed with water and dried over anhydrous magnesium sulfate. The dried solution is filtered and stripped of ether to yield the desired product O-[2-(N-3-allylphenylcarbamoyloxy)-2-methoxyiminoethyl] 3-methylsulfinylphenyl(4-methylthiophenyl)phosphinate.

EXAMPLE 22

Preparation of
1-Chloro-2-(N-2-dimethylaminophenylcarbamoyloxy) 2-methoxyiminoethane N-Methoxychloroacetamide (12.3 grams; 0.1 mole), benzene (60 ml) and dibutyltin dilaurate (1 drop) are charged into a glass reaction flask equipped with a mechanical stirrer, thermometer and reflux condenser. 2-Dimethylaminophenylisocyanate (16.2 grams; 0.1 mole) dissolved in benzene (30 ml) is incrementally added to the reaction mixture with stirring at room temperature. After the addition is completed the reaction mixture is heated at reflux for a period of about 3 hours. After this time the reaction mixture is distilled to remove benzene and unreacted starting material thereby yielding the desired product 1-chloro-2-(N-2-dimethylaminophenylcarbamoyloxy) 2-methoxyiminoethane.

EXAMPLE 23

Preparation of
O-[2-(N-2-Dimethylaminophenylcarbamoyloxy)-2-methoxyiminoethyl] O-Pent-3-enyl- S-Ethyl Thiolophosphate 1-Chloro-2-(N-2-dimethylaminophenylcarbamoyloxy)-2-methoxyiminoethane (14.2 grams; 0.05 mole), methyl ethyl ketone (80ml), potassium O-pent-3-enyl S-ethyl thiolophosphate (12.4 grams; 0.05 mole) and a few crystals of potassium iodide are charged into a glass reaction flask equipped with a mechanical stirrer, thermometer and reflux condenser. The reaction mixture is then heated at reflux for a period of about 4 hours. After this time the reaction mixture is cooled to room temperature and is filtered to remove inorganic salts. The salts are washed with acetone and the washings combined with the filtrate. The resulting solution is stripped of solvents in a rotary evaporator. The remaining residue is dissolved in ether and the ether solution is washed with water and dried over anhydrous magnesium sulfate. The dried solution is filtered and stripped of ether to yield the desired product O-[2-(N-2-dimethylaminophenylcarbamoyloxy)-2-methoxyiminoethyl] O-pent-3-enyl S-ethyl thiolophosphate.

EXAMPLE 24

Preparation of
1-Chloro-2-(N,N-dimethylcarbamoyloxy)-2-methoxyiminoethane

N-Methoxychloroacetamide (12.3 grams; 0.1 mole), benzene (75 ml) and triethylamine (12 grams; 1.2 mole) are charged into a glass reaction flask equipped with a mechanical stirrer, therometer and reflux condenser. N,N-Dimethylcarbamoyl chloride (11 grams; 0.1 mole) dissolved in benzene (25 ml) is incrementally added to the reaction mixture, with stirring, at room temperature. After the addition is completed the reaction mixture is heated at reflux for a period of about 3 hours. After this time the reaction mixture is distilled to remove benzene and unreacted starting material thereby yielding the desired product 1-chloro-2-(N,N-dimethylcarbamoyloxy)-2-methoxyiminoethane.

EXAMPLE 25

Preparation of
O-[2-(N,N-Dimethylcarbamoyloxy)-2-methoxyiminoethyl] O-Ethyl 2-Methyl-4-chlorobenzylphosphonate 1-Chloro-2-(N,N-dimethylcarbamoyloxy)-2-methoxyiminoethane (10grams; 0.05 mole), methyl ethyl ketone (60ml), potassium O-ethyl 2-methyl-4-chlorobenzylphosphonate (15.6 grams; 0.05 mole) and a few crystals of potassium iodide are charged into a glass reaction flask equipped with a mechanical stirrer, thermometer and reflux condenser. The reaction mixture is then heated at reflux for a period of about 4 hours. After this time the reaction mixture is cooled to room temperature and is filtered to remove inorganic salts. The salts are washed with acetone and the washings combined with the filtrate. The resulting solution is stripped of solvent in a rotary evaporator. The remaining residue is dissolved in ether and the ether solution is washed with water and dried over anhydrous magnesium sulfate. The dried solution is filtered and stripped of ether to yield the desired product O-[2-(N,,N-dimethylcarbamoyloxy)-2-methoxyiminoethyl] O-ethyl 2-methyl-4-chlorobenzylphosphonate.

EXAMPLE 26

Preparation of
1-Chloro-1-methyl-2-(N-methyl-N-cyclohexycarbamoyloxy)-2-methoxyiminoethane N-Methoxy-α-chloropropionamide (13.8 grams; 0.1 mole), benzene (70 ml) and triethylamine (12 grams; 0.12 mole) are charged into a glass reaction flask equipped with a mechanical stirrer, thermometer and reflux condenser. N-Methyl-N-cyclohexylcarbamoyl chloride (17.9 grams; 0.1 mole) dissolved in benzene (30 ml) is incrementally added to the reaction mixture, with stirring, at room temperature. After the addition is completed the reaction mixture is heated at reflux for a period of about 3 hours. After this time the reaction mixture is distilled to remove benzene and unreacted starting material thereby yielding the desired product 1-chloro-1-methyl-2-(N-methyl-N-cyclohexylcarbamoyloxy)-2-methoxyiminoethane.

EXAMPLE 27

Preparation of
S-[1-Methyl-2-(N-methyl-N-cyclohexylcarbamoyloxy)-2-methoxyiminoethyl] S-[γ-(3-Allylphenyl)propyl] N,N-Diethyldithiolophosphoramidate 1-Chloro-1-methyl-2-(N-methyl-N-cyclohexylcarbamoyloxy)-2-methoxyiminoethane (15.0 grams; 0.05 mole), methyl ethyl ketone (60 ml), potassium S-[γ-3-allylphenyl)propyl] N,N-diethyldithiolophosphoramidate (17.5 grams; 0.05 mole) and a few crystals of potassium iodide are charged into a glass reaction flask equipped with a mechanical stirrer, thermometer and reflux condenser. The reaction mixture is then heated at reflux for a period of about 8 hours. After this time the reaction mixture is cooled to room temperature and is filtered to remove inorganic salts. The salts are washed with acetone and the washings combined with the filtrate. The resulting solution is stripped of solvents in a rotary evaporator. The remaining residue is dissolved in ether and the ether solution is washed with water and dried over anhydrous magnesium sulfate. The dried solution is filtered and stripped of ether to yield the desired product S-[1-methyl-2-(N-methyl-N-cyclohexylcarbamoyloxy)-2-methoxyiminoethyl] S-[γ-(3-allylphenyl)propyl] N,N-diethyldithiolophosphoramidate.

EXAMPLE 28

Preparation of
1-Chloro-1-(4-chlorophenyl)-2-(N,N-diethylcarbamoyloxy)-2-methoxyiminoethane N-Methoxy-α-(4-chlorophenyl)-α-chloroacetamide (23.3 grams; 0.1 mole), benzene (100 ml), and triethylamine (12 grams; 0.12 mole) are charged into a glass reaction flask equipped with a mechanical stirrer, thermometer and reflux condenser. N,N-Diethylcarbamoyl chloride (13.5 grams; 0.1 mole) dissolved in benzene (25 ml) is incrementally added to the reaction mixture, with stirring, at room temperature. After the addition is completed the reaction mixture is heated at reflux for a period of about 4 hours. After this time the reaction mixture is distilled to remove benzene and unreacted starting material thereby yielding the desired product 1-chloro-1-(4-chlorophenyl)-2-(N,N-diethylcarbamoyloxy)-2-methoxyiminoethane.

EXAMPLE 29

Preparation of O-[1-(4-Chlorophenyl)-2-(N,N-diethylcarbamoyloxy)-2-methoxyiminoethyl] O,O-Diethyl Phosphate 1-Chloro-1-(4-chlorophenyl)-2-(N,N-diethylcarbamoyloxy)-2-methoxyiminoethane (16.6 grams; 0.05 mole), methyl ethyl ketone (100 ml), potassium O,O-diethyl phosphate (9.6 grams; 0.05 mole) and a few crystals of potassium iodide are charged into a glass reaction flask equipped with a mechanical stirrer, thermometer and reflux condenser. The reaction mixture is then heated at reflux for a period of about 12 hours. After this time the reaction mixture is cooled to room temperature and is filtered to remove inorganic salts. The salts are washed with acetone and the washings combined with the filtrate. The resulting solution is stripped of solvents in a rotary evaporator. The remaining residue is dissolved in ether and the ether solution is washed with water and dried over anhydrous magnesium sulfate. The dried solution is filtered and stripped of ether to yield the desired product O-[1-(4-chlorophenyl)-2-(N,N-diethylcarbamoyloxy)-2-methoxyiminoethyl] O,O-diethyl phosphate.

Additional compounds within the scope of the present invention which can be prepared by the procedures of the foregoing examples are as follows: S-(2-carbamoyloxy-2-methoxyiminoethyl) O,O-diethyl thiolothionophosphate, S-(2-carbamoyloxy-2-methoxyiminoethyl) O,O-diethyl thiolophosphate, S-[2-(N-methylcarbamoyloxy)-2-methoxyiminoethyl] O,O-diethyl thiolophosphate, S-[2-(N-butylcarbamoyloxy)-2-methoxyiminoethyl] O,O-dipropyl thiolothionophosphate, S-[2-hexylcarbamoyloxy-2-methoxyiminoethyl] O-(2-ethylphenyl) O-(4-fluorophenyl) thiolothionophosphate, S-[2-(N-cyclobutylcarbamoyloxy)-2-methoxyiminoethyl] O-(3-allylphenyl) O-(2-ethoxyphenyl) thiolothionophosphate, S-[2-(N-cyclopentylcarbamoyloxy)-2-methoxyiminoethyl] O-(4-butylphenyl) O-(4-hexylphenyl) thiolothionophosphate, S-[2-(N-cycloheptylcarbamoyloxy)-2-methoxyiminoethyl] O-(3-propoxyphenyl) O-(4-iodophenyl) thiolothionophosphate, S-[1-methoxy-2-(N-methylcarbamoyloxy)-2-methoxyiminoethyl] O-(4-pent-3-enylphenyl) O-(3-hexyloxyphenyl) thiolothionophosphate, S-[1-ethoxy-2-(N-methylcarbamoyloxy)-2-methoxyiminoethyl] O-(4-ethylthiophenyl) O-(4-trichloromethyl) thiolothionophosphate, S-[1-propoxy-2-(N-methylcarbamoyloxy)methoxyiminoethyl] O,O-dimethyl thiolothionophosphate, S-[1-hexyloxy-2-(N-methylcarbamoyloxy)-2-methoxyiminoethyl] O,O-dimethyl thiolothionophosphate, S-{1-(2-methylphenyl)-2-[N-(4-isopropylphenyl)carbamoyloxy]-2-methoxyiminoethyl } O,O-diethyl thiolophosphate, S-{--(3-propylphenyl)-2-[N-(4-bromophenyl)carbamoyloxy]-2-methoxyiminoethyl} O,O-diethyl thiolophosphate, S-{1-(4-pentylphenyl)-2-[N-(4-fluorophenyl)carbamoyloxy]-2-methoxyiminoethyl } O,O-diethyl thiolophosphate, O-[2-(N-methylcarbamolyoxy)-2-methoxyiminoethyl] O-ethyl methylphosphonate, S-[2-(N-methylcarbamoyloxy)-2-methoxyiminoethyl] O-ethyl ethylthiolophosphonate, S-[2-(N,N-dimethylcarbamoyloxy)-2-methoxyiminoethyl] O-ethyl ethylthiolophosphonate, S-[2-(N,N-dimethylcarbamoyloxy)-2-methoxyiminoethyl] O-phenyl ethylthiolophosphonate, S-[2-N,N-dimethylcarbamoyloxy)-2-methoxyiminoethyl] O-(4-ethylsulfonylphenyl) ethylthiolophosphonate, S-[2-(N,N-dimethylcarbamoyloxy)-2-methoxyiminoethyl] O-(3-propylsulfonylphenyl) ethylthiolophosphonate, S-[2-(N,N-dimethylcarbamoyloxy)-2-methoxyiminoethyl] O-(4-hexylsulfonylphenyl) ethylthiolophosphate, S- 1-methylthio-2-[N-(4-ethoxyphenyl)carbamoyloxy]-2-methoxyiminoethyl O-(2-propylthiophenyl) ethylthiolophosphonate, S-{1-(4-bromophenyl)-2-[N-(4-propoxyphenyl)carbamoyloxy]-2-methoxyiminoethyl} O-(2-hexylthiophenyl) ethylthiolophosphonate, S-{1-(4-fluorophenyl)-2-[N-(4-hexyloxyphenyl)carbamoyloxy]-2-methoxyiminoethyl } O-(3-propylsulfinylphenyl) ethylthiolophosphonate, S-{1-(2-dimethylaminophenyl)-2-[N-(4-trifluoromethylphenyl)carbamoyloxy]-2-methoxyiminoethyl} O-(-dipropylaminophenyl) ethylthiolophosphonate, S-{ 1-(2-methylsulfonylphenyl)-2-[N-(3-allylphenyl)-carbamoyloxy]-2-methoxyiminoethyl } O-(4-dihexylaminophenyl) ethylthiolophosphonate, O-{1-(4-dipropylaminophenyl)-2-[N-(4-ethylthiophenyl)-carbamoyloxy]-2-methoxyiminoethyl } (4-hexylsulfinylphenyl)ethylphosphinate, O-{1-(3-nitrophenyl)-2-[N-(4-propylthiophenyl)carbamoyloxy]-2-methoxyiminoethyl } (3,4-dichlorophenyl)propylphosphinate, O-{1-(2-methoxyphenyl)-2-[N-(3-hexylphenyl)carbamoyloxy]-2-methoxyiminoethyl } dibutylphosphinate, S- {1-(4-ethoxyphenyl)-2-[N-(4-pent-3-enylphenyl)carbamoyloxy]-2-methoxyiminoethyl} dihexylthiolophosphinate, S-{1-(4-propoxyphenyl)-2-[N-(4-propylthiophenyl)carbamoyloxy]-2-methoxyiminoethyl } diethylthiolothionophosphinate, S-{1-(3-hexyloxyphenyl)-2-[N-(4-hexylthiophenyl)carbamoyloxy)-2-methoxyiminoethyl } dipropylthiolothionophosphinate, O-{1-(3-methylthiophenyl)-2 -[N-(4-trichloromethylphenyl)carbamoyloxy]-2-methoxyiminoethyl } dimethylthionophosphinate, O-{1-(4-ethylthiophenyl)-2-[N-(4-iodophenyl)carbamoyloxy]-2-methoxyiminoethyl } dimethylthionophosphinate, O-{1-(3-propylthiophenyl)-2-[N-(4-diethylaminophenyl)carbamoyloxy]-2-methoxyiminoethyl } dimethylthionophosphinate, S-{1-(4-butylthiophenyl)-2-]N-(3-dibutylaminophenyl)carbamoyloxy]-2-methoxyiminoethyl } diethylthiolophosphinate, S-{1-(4-hexylthiophenyl)--hexylthiophenyl)-2-[N-(4-dihexylaminophenyl)carbamoyloxy]-2-methoxyiminoethyl } diethylthiolophosphinate, S-{1-(4-iodophenyl)-2-[N-(2-ethyl-4-chlorophenyl)-carbamoyloxy]-2-methoxyiminoethyl } diethylthiolophosphinate, S-[1-(2-allylphenyl)-2-(N,N-dimethylcarbamoyloxy)-2-methoxyiminoethyl] diethylthiolophosphinate, S-[1-(4-trifluoromethylphenyl)-2-(N,N-dimethylcarbamoyloxy)-2-methoxyiminoethyl] diethylthiolophosphinate, S-[1-(4-trichloroethylphenyl)-2-(N,N-dimethylcarbamoyloxy)-2-methoxyiminoethyl] diethylthiolophosphinate, S-[1-(3-β-bromoethylphenyl)-2-(N,N-dimethylcarbamoyloxy)-2-methoxyiminoethyl] diethylthiolophosphinate, S-[1-(2-pent-3-enylphenyl)-2-(N,N-dimethylcarbamoyloxy)-2-methoxyiminoethyl] diethylthiolophosphinate, S-[1-(4-methylsulfonylphenyl)-2-(N,N-dimethylcarbamoyloxy)-2-methoxyiminoethyl] diethylthiolophosphinate, S-[1-(4-ethylsulfonylphenyl)-2-(N,N-dimethylcarbamoyloxy)-2-methoxyiminoethyl] diethylthiolophosphinate, S-[1-(4-propylsulfonylphenyl)-2-(N,N-dimethylcarbamoyloxy)-2-methoxyiminoethyl] diethylthiolophosphinate, S-[1-(4-hexylsulfonylphenyl)-2-(N,N-dimethylcarbamoyloxy)-2-methoxyiminoethyl] diethylthiolophosphinate, S-[1-(3-methylsulfinylphenyl)-2-(N,N-dimethylcarbamoyloxy)-2-methoxyiminoethyl] diethylthiolophosphinate, S-[1-(3-ethylsulfinylphenyl)-2-(N,N-dimethylcarbamoyloxy)-2-methoxyiminoethyl] diethylthiolophosphinate, S-[1-(4-propylsulfinylphenyl)-2-(N,N-dimethylcarbamoyloxy)-2-methoxyiminoethyl] diethylthiolophosphinate, S-[1-(4-hexylsulfinylphenyl)-2-(N,N-dimethylcarbamoyloxy)-2-methoxyiminoethyl] diethylthiolophosphinate, S-[1-(4-dihexylaminophenyl)-2-(N,N-dimethylcarbamoyloxy)- 2-methoxyiminoethyl] diethylthiolophosphinate, O-[1-phenoxy-2-(N-methylcarbamoyloxy)-2-methoxyiminoethyl] O-ethyl N-methylphosphoramidate, O-[1-phenylthio-2-(N-methylcarbamoyloxy)-2-methoxyiminoethyl] O-butyl N-ethylphosphoramidate, O-[1-methylthio-2-(N-methylcarbamoyloxy)-2-methoxyiminoethyl] O-hexyl N-hexylphosphoramidate, O-[1-ethylthio-2-(N-methylcarbamoyloxy)-2-methoxyiminoethyl] O-allyl N,N-dipropylphosphoramidate, O-[1-butylthio-2-(N-methylcarbamoyloxy)-2-methoxyiminoethyl] O-pent-3-enyl N,N-dibutyl, S-[1-(3,4-dichlorobenzyl)-2-(N-methylcarbamoyloxy)-2-methoxyiminoethyl] S-methyl N-isopropyldithiolophosphoramidate, S-[2-(N-methylcarbamoyloxy)-2-methoxyiminoethyl] S-ethyl N-t-butyldithiolophosphoramidate, S-[2-(N-methylcarbamoyloxy)-2-methoxyiminoethyl] S-propyl N-isopropyldithiolophospohoramidate, S-[2-(N-methylcarbamoyloxy)-2-methoxyiminoethyl] S-butyl N-isopropyldithiolophosphoramidate, S-[2-(N-methylcarbamoyloxy)-2-methoxyiminoethyl] S-hexyl N-isopropyldithiolophosphoramidate, S-[2-(N-methylcarbamoyloxy)-2-methoxyiminoethyl] methyl-N-isopropylthiolophosphonamidate, S-[2-(N-methylcarbamoyloxy)-2-methoxyiminoethyl] ethyl-N-t-butylthiolophosphonamidate, S-[2-(N-methylcarbamoyloxy)-2-methoxyiminoethyl] propyl-N-ethylthiolophosphonamidate, S-[2-(N-methylcarbamoyloxy)-2-methoxyiminoethyl] hexyl-N-isopropylthiolothionophosphinate, and the like.

For practical use as insecticides or acaricides, the compounds of this invention are generally incorporated into insecticidal or acaricidal compositions which comprise an inert carrier and an insecticidally or acaricidally toxic amount of such a compound. Such insecticidal or acaricidal compositions, which can also be called formulation, enable the active compound to be applied conveniently to the site of the insect or acarid infestation in any desired quantity. These compositions can be solids such as dusts, granules or wettable powders; or they can be liquids such as solutions, aerosols or emulsifiable concentrates.

For example, dusts can be prepared by grinding and blending the active compound with a solid inert carrier such as the talcs, clays, silicas, pyrophyllite and the like. Granular formulations can be prepared by impregnating the compound, usually dissolved in a suitable solvent, onto and into granulated carriers such as the attapulgites or the vermiculites, usually of a particle size range of from about 0.3 to 1.5 mm. Wettable powders, which can be dispersed in water and/or oil to any desired concentration of the active compound, can be prepared by incorporating wetting agents into concentrated dust compositions.

In some cases the active compounds are sufficiently soluble in common organic solvents such as kerosene or xylene so that they can be used directly as solutions in these solvents. Frequently, solutions of insecticides or acaricides can be dispersed under superatmospheric pressure as aerosols. However, preferred liquid insecticidal or acaricidal compositions are emulsifiable concentrates, which comprise an active compound according to this invention and as the inert carrier, a solvent and an emulsifier. Such emulsifiable concentrates can be extended with water and/or oil to any desired concentration of active compound for application as sprays to the site of the insect or acarid infestation. The emulsifiers most commonly used in these concentrates are nonionic or mixtures of nonionic with anionic surface-active agents.

A typical insecticidal or acaricidal composition according to this invention is illustrated by the following example, in which the quantities are in parts by weight.

EXAMPLE 30

Preparation of a Dust

| | |
|---|---|
| Product of Example | 10 |
| Powdered talc | 90 |

The above ingredients are mixed in a mechanical grinder-blender and are ground until a homogeneous, freeflowing dust of the desired particle size is obtained. This dust is suitable for direct application to the site of the insect or acarid infestation.

The compounds of this invention can be applied as insecticides or acaricides in any manner recognized by the art. One method for destroying insects or acarids comprises applying to the locus of the insect or acarid infestation, an insecticidal or acaricidal composition comprising an inert carrier and, as an essential active ingredient, in a quantity which is toxic to said insects or acarids, a compound of the present invention. The concentration of the new compounds of this invention in the insecticidal or acaricidal compositions will vary greatly with the type of formulation and the purpose for which it is designed, but generally the insecticidal or acaricidal compositions will comprise from about 0.05 to about 95 percent by weight of the active compounds of this invention. In a preferred embodiment of this invention, the insecticidal or acaricidal compositions will comprise from about 5 to 75 percent by weight of the active compound. The compositions can also comprise such additional substances as other pesticides, stabilizers, spreaders, deactivators, adhesives, stickers, fertilizers, activators, synergists and the like.

The compounds of the present invention are also useful when combined with other insecticides or acaricides in the compositions heretofore described. These other insecticides or acaricides can comprise from about 5 to about 95% of the active ingredients in the compositions. Use of the combinations of these other insecticides or acaricides with the compounds of the present invention provide insecticidal and/or acaricidal compositions which are more effective in controlling insects or acarids and often provide results unattainable with separate compositions of the individual compounds. The other insecticides or acaricides with which the compounds of this invention can be used in the insecticidal or acaricidal compositions to control insects or acarids include halogenated compounds such as DDT, methoxychlor, TDE, lindane, chlordane, isobenzan, aldrin, dieldrin, heptachlor, endrin, mirex, endosulfon, dicolfol and the like; organic phosphorus compounds such as TEPP, schradan, ethion, parathion, methyl parathion, EPN, demeton, carbophenothion, phorate, zinophos, diazinon, malathion mevinphos, dimethoate, DBD, ronnel, oxydemeton-methyl, dicapthon, chlorothion, phosphamidon, naled, fenthion, trichlorofon, DDVP and the like; organic nitrogen compounds such as dinitro-o-cresol, dinitrocyclohexylphenol, DNB. DNP, binapacril, azobenzene and the like; organic carbamate compounds such as carbaryl, ortho 5353 and the like; organic sulfur compounds such as phenothiazine, phenoxathin, lauryl thiocyanate, bis(2-thiocyanoethyl)ether, isobornyl thiocyanoacetate and the like; as well as such substances usually referred to as fumigants as hydrogen cyanide, carbon tetrachloride, calcium cyanide, carbon disulfide, ethylene dichloride, propylene dichloride, ethylene dibromide, ethylene oxide, methyl bromide, paradichlorobenzene and the like.

The compounds of the present invention can also be combined with fungicidal and nematocidal chemical compounds to form pesticidal compositions useful for the control of fungi and in some cases soil nematodes as well as insects or acarids. Typical examples of such fungicidal chemical compounds are ferbam, nabam, zineb, ziram, thiram, chloranil, dichlone, glyodin, cycloheximide, dinocap, maneb, captan, dodine, PCNB, p-dimethylaminobenzenediazo sodium sulfonate and the like; while examples of nematocidal compounds are chloropicrin, O,O-diethyl O-(2,4-dichlorophenyl) phosphorothioate, tetrachlorothiophene, dazomet, dibromochloropropane and the like.

The new compounds of this invention can be used in many ways for the control of insects or acarids. Insecticides or acaricides which are to be used as stomach poisons or protective materials can be applied to the surface on which the insects or acarids feed or travel. Insecticides or acaricides which are to be used as contact poisons or eradicants can be applied directly to the body of the insect or acarid, as a residual treatment to the surface on which the insect or acarid may walk or crawl, or as a fumigant treatment of the air which the insect or acarid breathes. In some cases, the compounds applied to the soil or plant surfaces are taken up by the plant, and the insects or acarids are poisoned systemically.

The above methods of using insecticides are based on the fact that almost all the injury done by insects is a direct or indirect result of their attempts to secure food. Indeed, the large number of destructive insects can be classified broadly on the basis of their feeding habits. Among the insects which can be effectively controlled by the compounds of the present invention are the chewing insects, such as the Mexican bean beetle and the southern armyworm; the piercing-sucking insects, such as the pea aphid, the cereal leaf beetle, the housefly, the grape leafhopper, the chinch bug, the lygus bug, the oyster shell scale, the California red scale, the Florida red scale, the soft scale and mosquitoes; the internal feeders, including borers, such as the European corn borer, the peach twig borer and the corn earworm, worms or weevils, such as the codling moth, the alfalfa weevil, the cotton boll weevil, the pink boll worm, the plum curculio, the red banded leaf roller, the melonworm, the cabbage looper and the apple maggot, leaf miners, such as the apple leaf miner, the birch leaf miner and the beet leaf miner, and gall insects, such as the wheat joint worm and the grape phylloxera. Insects which attack below the surface of the ground are classified as subterranean insects and include such destructive pests as the wooly apple aphid, the Japanese beetle, the onion maggot and the corn rootworm.

Mites and ticks are not true insects. Many economically important species of mites and ticks can be controlled by the compounds of this present invention, such as the red spider mite, the two-spotted mite, the strawberry spider mite, the citrus rust mite, the cattle tick, the poultry mite, the citrus red mite and the European red mite. Chemicals useful for the control of mites are often called miticides, while those useful for the control of both mites and ticks are known specifically as acaricides.

The quantity of active compound of this invention to be used for insect or acarid control will depend on a variety of factors, such as the specific insect involved, intensity of the infestation, weather, type of environment, type of formulation and the like. For example, the application of only one or two ounces of active chemical per acre may be adequate for control of a light infestation of an insect or acarid under conditions unfavorable for its feeding, while a pound or more of active compound per acre may be required for the control of a heavy infestation of insects or acarids under conditions favorable to their development.

The insecticidal and acaricidal activity of the compounds of the present invention was demonstrated in experiments carried out for the control of a variety of insects at various concentrations. The test procedures and the results are shown below.

MEXICAN BEAN BEETLE - STOMACH POISON

Foliar portions of potted Dwarf Horticultural bean plants in first true leaf growth stage are dipped in agitated test solution containing the compound of this invention, allowed to air dry and removed to holding racks provided with a subterranean water source. Three test plants are used for each test unit. Five third-instar larvae of Mexican Bean Beetle are caged on treated plants for 72 hours. After this time observations are made for insect mortality.

TWO-SPOTTED SPIDER MITE - CONTACT POISON

Potted horticultural beans at growth stage when primary leaves are approximately one inch long are infested with two-spotted spider mites twenty-four (24) hours prior to treatment, insuring establishment of adults and egg deposition at time of treatment.

The candidate compound is dissolved in a suitable solvent (acetone, methanol or other) or prepared as wettable powders and diluted to appropriate concentration with deionized water containing wetting and/or dispersing agents as appropriate.

Infested host plants, as above, are dipped in agitated solution of the candidate compound, allowed to air dry, provided with subterrranean water source and held for observation. Three plants are used for each unit of treatment.

Initial mortality and phytotoxicity are determined forty-eight (48) to seventy-two (72) hours after treatment by removing and observing one leaf from each plant. Final observations of mortality are made seven (7) days after treatment by removal and observation of the second primary leaf.

HOUSEFLY - LIQUID BAIT

The candidate compound is prepared as an acetone or wettable powder-based aqueous formulation containing 5 percent (W:V) dissolved granular sugar. One milliliter, expressed in ppm active ingredient, is pipetted onto the center of a 9 cm petri dish. Two-day old housefly adults, loaded into a 4-inch hemispherical wire mesh container, are then caged over the liquid bait. Approximately six (6) hours later a water-moistened wad of cellucotton is placed on top of the wire mesh cage and retained there overnight.

Observations are made for 24-hour mortality. Mortality induced may be by ingestion, contact or repellent-induced starvation.

BOLL WEEVIL - LIQUID BAIT

The candidate compound is prepared as an acetone or wettable powder-based aqueous formulation containing 5 percent (W:V) dissolved granular sugan. One milliliter, expressed in ppm active ingredient, is pipetted onto a 9 cm filter paper in a 9 cm petri dish. Five (5) Boll Weevil adults are introduced and the petri dish cover affixed.

Observations are made for mortality after 72 hours. Mortality induced may be by contact, ingestion or fumigant action.

TWO-SPOTTED SPIDER MITE - SYSTEMIC ACTION

Cranberry bean plants grown under greenhouse conditions, in first true leaf growth stage and in soil of low moisture content are infested during a two-hour period with Two-Spotted Spider Mites (*Tetranychus telarius*). Twenty ml. of an aqueous solution of the candidate compound at a desired concentration is applied to the soil as a surface drench. Twenty-four hours later plants are provided subterranean watering for 48 hours. Percentage mite mortality is observed 96 hours after application of the candidate compound to the soil surface. All test units are in triplicate.

MEXICAN BEAN BEETLE - SYSTEMIC ACTION

Cranberry bean plants grown under greenhouse conditions, in the first true leaf stage and in soil of low moisture content are treated with 20 ml. of an aqueous solution of the test compound at a desired concentration. Thereafter the bean plants are infested with Mexican Bean Beetles. The plants are supplied with water and light as required. After a period of several days the insect mortality is observed.

TABLE I

TEST RESULTS
Percent Control
Insect and Test Procedure*

| Test Compound | Concentration ppm | MBB-SP | TSM-C | HF-B | BW-B | TSM-S | MBB-S |
|---|---|---|---|---|---|---|---|
| Product of Ex. 2 | 1000 | 30 | 100 | 100 | 100 | — | — |
| " | 500 | — | 100 | 100 | 100 | — | — |
| " | 250 | — | 100 | 100 | 100 | — | — |
| " | 100 | — | 96 | 100 | 100 | — | — |
| " | 50 | — | — | — | — | 84 | 100 |
| " | 25 | — | — | — | — | 68 | 10 |
| Product of Ex. 3 | 1000 | 100 | 100 | 100 | 100 | — | — |
| " | 500 | 100 | 100 | 100 | 100 | — | — |
| " | 250 | 100 | 100 | 100 | 100 | — | — |
| " | 100 | 30 | 100 | 100 | 100 | — | — |
| " | 50 | — | — | — | — | 100 | 100 |
| " | 25 | — | — | — | — | 100 | 70 |
| " | 10 | — | — | — | — | 100 | 70 |
| " | 5 | — | — | — | — | 100 | 10 |

*MBB-SP = Mexican Bean Beetle - Stomach Poison
TSM-C = Two-Spotted Spider Mite - Contact Poison
HF-B = Housefly - Bait
BW-B = Boll Weevil - Bait
TSM-S = Two-Spotted Spider Mite - Systemic
MBB-S = Mexican Bean Beetle - Systemic

I claim:
1. An insecticidal or acaricidal composition comprising an inert carrier and, as an essential active ingredient, in a quantity toxic to insects or acarids, a compound of the formula

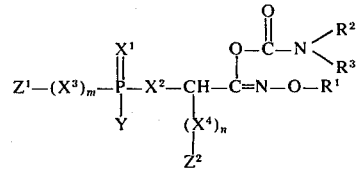

wherein $R^1$ is lower alkyl; $R^2$ is selected from the group consisting of hydrogen, lower alkyl, lower alkenyl and lower haloalkyl; $R^3$ is selected from the group consisting of hydrogen, lower alkyl, lower alkenyl, lower haloalkyl, cycloalkyl of from 3 to 7 carbon atoms and

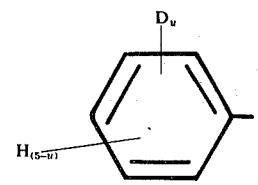

wherein D is selected from the group consisting of lower alkyl, lower alkenyl, lower alkoxy, lower alkylthio, chlorine, bromine, fluoring, lower haloalkyl, nitro and di(lower alkyl)amino; u is an integer from 0 to 3; $X^1$, $X^2$, $X^3$ and $X^4$ are independently selected from the group consisting of oxygen and sulfur; m and n are each integers from 0 to 1; $Z^1$ is selected from the group consisting of lower alkyl, lower alkenyl and

23

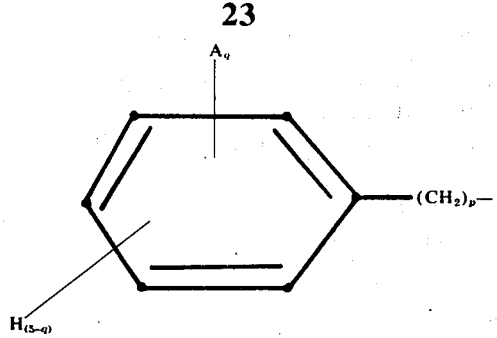

wherein A is selected from the group consisting of lower alkyl, lower alkenyl, lower alkoxy, lower alkylthio, lower haloalkyl, chlorine, bromine, fluoring, nitro, lower alkylsulfoxide, lower alkylsulfone and di(lower alkyl)amino; and q and p are each integers from 0 to 3; $Z^2$ is selected from the group consisting of hydrogen and $Z^1$, provided that when $Z^2$ is hydrogen then n is zero; and Y is selected from the group consisting of lower alkyl, lower alkenyl, lower alkoxy, lower alkenyloxy, lower alkylthio, amino, lower alkylamino, di(lower alkyl)amino and

24

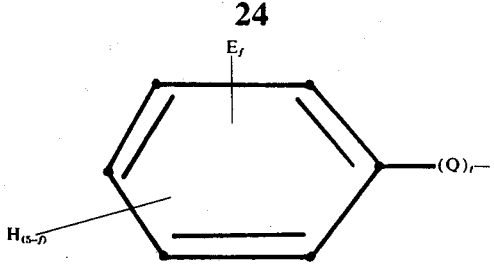

wherein E is selected from the group consisting of lower alkyl, lower alkenyl, lower alkoxy, lower alkylthio, chlorine, bromine fluorine, nitro, lower alkylsulfoxide, lower alkylsulfone and di(lower alkyl)amino; f is an integer from 0 to 3; Q is selected from the group consisting of oxygen, sulfur, lower alkylene, lower alkyleneoxy and lower alkylenethio; and t is an integer from 0 to 1.

2. A method of destroying insects which comprises constacting said insects with an insecticidal composition of claim 1 in a quantity which is toxic to said insects.

3. A method of destroying acarids which comprises contacting said acarids with an acaricidal composition of claim 1 in a quantity which is toxic to said acarids.

* * * * *